(12) United States Patent
Dodson et al.

(10) Patent No.: US 10,392,410 B2
(45) Date of Patent: Aug. 27, 2019

(54) PROCESSES FOR FRACTIONATING PHOSPHOLIPIDS

(71) Applicant: Archer Daniels Midland Company, Decatur, IL (US)

(72) Inventors: Greg Dodson, Decatur, IL (US); Doug Geier, Decatur, IL (US); John G. Soper, Mt. Zion, IL (US); Kristen Eilts, Decatur, IL (US)

(73) Assignee: Archer Daniels Midland Company, Decatur, IL (US)

( * ) Notice: Subject to any disclaimer, the term of this patent is extended or adjusted under 35 U.S.C. 154(b) by 0 days.

(21) Appl. No.: 15/532,326

(22) PCT Filed: Dec. 4, 2015

(86) PCT No.: PCT/US2015/064009
§ 371 (c)(1),
(2) Date: Oct. 17, 2017

(87) PCT Pub. No.: WO2016/090256
PCT Pub. Date: Jun. 9, 2016

(65) Prior Publication Data
US 2018/0125091 A1    May 10, 2018

Related U.S. Application Data

(60) Provisional application No. 62/088,126, filed on Dec. 5, 2014.

(51) Int. Cl.
*C07F 9/10* (2006.01)
*A23J 7/00* (2006.01)
*C11B 3/10* (2006.01)

(52) U.S. Cl.
CPC ............... *C07F 9/103* (2013.01); *A23J 7/00* (2013.01); *C11B 3/10* (2013.01)

(58) Field of Classification Search
CPC ............... C07F 9/103; C11B 3/10; A23J 7/00
See application file for complete search history.

(56) References Cited

U.S. PATENT DOCUMENTS 2,945,869 A    7/1960    Meyer
4,235,793 A *  11/1980  Betzing ................... C07F 9/103
                                                554/83

(Continued)

FOREIGN PATENT DOCUMENTS

| AU | 1984023916 | * | 1/1984 | ............... A23J 7/02 |
|---|---|---|---|---|
| AU | 1984023916 | | 8/1984 | |
| CN | 102146094 | | 8/2011 | |
| JP | PCT/JP87/00077 | | 8/1987 | |
| WO | 2015/0066268 | | 5/2015 | |

OTHER PUBLICATIONS

Liu, Daicheng et al; "22 Soybean Phospholipids", Oct. 28, 2011 (Oct. 28, 2011), pp. 483-501, XP055208001, Retrieved from the Internet: URL:http//cdn.intechopen.com/pdfs-wm/22616.pdf.

(Continued)

*Primary Examiner* — Yate' K Cutliff
(74) *Attorney, Agent, or Firm* — Andrew F. Nilles

(57) ABSTRACT

Processes of fractionating phospholipids are disclosed. In one embodiment, the process includes placing a phospholipid containing material in contact with an adsorbent, such that the adsorbent associates with at least one phospholipid of the phospholipid containing material. The process may further include eluting the at least one phospholipid from the adsorbent.

16 Claims, 17 Drawing Sheets

(56) References Cited

U.S. PATENT DOCUMENTS

| | | | |
|---|---|---|---|
| 4,528,139 A | 7/1985 | Napp | |
| 4,847,015 A * | 7/1989 | Shigematsu | A23J 7/00 554/83 |
| 5,214,171 A * | 5/1993 | Dijkstra | A23J 7/00 554/83 |

OTHER PUBLICATIONS

Liu, Yuanfa et al; "Purification of Soybean Phosphatidylcholine Using D113-III Ion Exchange Macroporous Resin Column Chromatography"; J Am Oil Chem Soc (2009) 86:183-188.

John, Johnson V.; "Simultaneous Extraction of Phosphatidylcholine and Phosphatidylethanolamine from Soybean Lecithin"; European Journal of Lipid Science and Technology, 2015 WILEY-VCH, Accepted: Mar. 9, 2015.

Patil, Vilas V. et al; "Extraction and purification of phosphotidylcholine from soyabean lecithin"; Separation and Purification Technology 75 (2010) 138-144.

Jangle, Rahul D. et al; "Phosphotidylcholine and its purification from raw de-oiled soya lecithin". Separation and Purification Technology 102 (2013) 287-195.

Liu Yan et al; "Separation and purification of phospholipids from soy molasses". China Oils and Fats vol. 33, No. 6 (2008) 61-64.

Meulenaer, B. De et al; "Optimization of Chromatographic Method for the Gram-Scale Preparative Fractionation of Soybean Phospholipids". Chromatographia vol. 41, No. 9/10 (Nov. 1995).

* cited by examiner

PROCESSES FOR FRACTIONATING PHOSPHOLIPIDS

TECHNICAL FIELD

The present invention relates generally to phospholipids and more particularly, to processes of purifying and/or fractionating phospholipids.

BACKGROUND OF THE INVENTION

Lecithin is a commercial by-product of vegetable oil production and is typically obtained from vegetable oils such as soybean oil, canola oil, sunflower oil, or corn oil. The high phospholipid content of lecithin makes it a natural emulsifier, stabilizer, baking improver, and wetting agent.

The mains phospholipids in lecithin are phosphatidyl choline (PC), phosphatidyl ethanolamine (PE), phosphatidyl inositol (PI), and phosphatidic acid (PA). The purified phospholipids, in particular PC, are often desired since they are value added nutritional and/or pharmaceutical compounds. Various methods have been developed to purify these phospholipids.

Some of the current methods of purifying the individual phospholipids use lecithin as a starting point. While these methods may be effective at purifying the phospholipids from the lecithin, the resulting products are the purified phospholipids and "phospholipid depleted" lecithin. A drawback of these methods is that while a higher value phospholipid may be obtained, the value of the lecithin itself may be of lower value since it has been depleted of the high-value phospholipid.

Thus, needs exists for improved methods of fractionating and/or purifying phospholipids, yet keeping the value of the various products associated with the process.

SUMMARY OF THE INVENTION

In each of its various embodiments, the present invention fulfills these needs and discloses processes of fractionating phospholipids.

In one embodiment, a method of fractionating phospholipids comprises placing a phospholipid containing material in contact with an adsorbent, such that the adsorbent associates with at least one phospholipid of the phospholipid containing material.

In each of the various embodiments of the present invention, the adsorbent may be a polymeric resin and may be selected from the group consisting of a phenolic resin, a styrene resin, a non-ionic resin, an acrylic resin, a cation-exchange resin, a weak-base resin, and combinations of any thereof. In each of the embodiments, the polymeric resin may also be a styrene resin or a phenolic resin.

In each of the embodiments of the present invention, the phospholipid containing material may be selected from the group consisting of miscella, molasses, lecithin, and combinations of any thereof. In the various embodiments, the phospholipid containing material may be miscella.

The method of fractionating phospholipids of the present invention may also include eluting the at least one phospholipid from the adsorbent which may be done by comprises an elution solvent with the adsorbent. The phospholipid containing material may contain less than 5% by weight of phospholipids and the at least one phospholipid eluted from the adsorbent contains more than 50% by weight of the phospholipids.

The method of fractionating phospholipids of the present invention may also include placing the at least one phospholipid eluted from the adsorbent in contact with a second adsorbent, which may optionally include mixing the at least one phospholipid eluted from the adsorbent with a solvent before placing in contact with the second adsorbent. The methods of fractionating phospholipids of the present invention may further comprise collecting the eluted, at least one phospholipid.

The methods of fractionating phospholipids of the present invention may further include mixing a solvent with the phospholipid containing material, thus producing a feed, where placing the phospholipid containing material in contact with the adsorbent comprises placing the feed in contact with the adsorbent. The methods may further comprise eluting the at least one phospholipid from the adsorbent with an elution solvent and/or collecting the eluted, at least one phospholipid and the elution solvent. The methods may also allow a precipitate to form in the eluted, at least one phospholipid and the elution solvent, and may include removing the precipitate from the eluted, at least one phospholipid and the elution solvent and concentrating the at least one phospholipid in the elution solvent.

In each of the various embodiments of the present invention, the solvent may selected from the group consisting of an alcohol, an alkane, water, and combinations of any thereof and the at least one phospholipid may be selected from the group consisting of phosphatidyl choline (PC), phosphatidyl ethanolamine (PE), phosphatidyl inositol (PI), phosphatidic acid (PA), and combinations of any thereof.

The methods of the present invention may also include extracting the phospholipid containing material from a phospholipid source, adjusting a pH of the phospholipid containing material to a pH of between 8.5-10.0, and/or removing solids from the phospholipid containing material.

In the various embodiments of the present invention, the adsorbent may located in a simulated moving bed chromatography system.

In various embodiment, the solvent used in the present invention may be the alkane and selected from the group consisting of hexane, heptane, or a combination thereof.

The phospholipids of the present invention may originate from a source selected from the group consisting of soybean, egg, canola, sunflower, corn, and combinations of any thereof.

In the present invention, a process of fractionating phospholipids includes mixing a phospholipid containing material selected from the group consisting of miscella, lecithin, molasses, and combinations of any thereof with a solvent, thus producing a feed, placing the feed in contact in contact with a polymeric resin, such that the polymeric resin associates with at least one phospholipid of the phospholipid containing material, and eluting the at least one phospholipid from the polymeric resin with an elution solvent.

The polymeric resin used in the present invention may be selected from the group consisting of a phenolic resin and a styrene resin, and the solvent may comprise an alcohol, an alkane, water, and combinations of any thereof. The elution solvent may comprises an alcohol, an alkane, water, and combinations of any thereof.

DETAILED DESCRIPTION OF THE INVENTION

Processes of fractionating and/or purifying phospholipids are disclosed. In one embodiment, the process may include placing a phospholipid containing material in contact with an adsorbent, such that the adsorbent associates with at least one phospholipid of the phospholipid containing material. The process may further include eluting the at least one phospholipid from the adsorbent. The adsorbent may be a resin.

The process may further include mixing a solvent with the phospholipid containing material, thus producing a feed and placing the feed in contact with the adsorbent. The process may also include collected the eluted, at least one phospholipid. The adsorbent or resin may also be placed in a column.

The phospholipid containing material may be miscella, molasses, lecithin, or combinations of any thereof and may originate from a source such as soybean, egg, canola, sunflower, corn, or combinations of any thereof.

In a further embodiment, the process may include extracting the phospholipid containing material from a phospholipid source. The process may further comprise removing solids from the phospholipid containing material.

In yet a further embodiment, the adsorbent may be located in a simulated moving bed chromatography system.

In an additional embodiment, the phospholipid containing material may contain less than 5% by weight of phospholipids and the at least one phospholipid eluted from the adsorbent may contain more than 50% by weight of the phospholipids.

The phospholipid containing material may be any substance or compound capable of having phospholipids extracted or fractionated therefrom using a resin. To be placed in contact with the resin, the phospholipid containing material may be in a liquid form and/or suspended in a liquid. The phospholipid containing material may also originate from and/or be extracted from a phospholipid source. For example, a phospholipid containing material such as lecithin may be extracted from a phospholipid source such as soybeans. The lecithin may be crude lecithin, de-oiled lecithin, lecithin paste, or any other lecithin source. Examples of phospholipid sources include without limitation eggs or fractions thereof, and vegetable crops such as soybean, canola, sunflower, or corn or fractions thereof.

In an additional embodiment, the phospholipid containing material is not lecithin, and may be miscella, solubles, or molasses.

Figure 1:
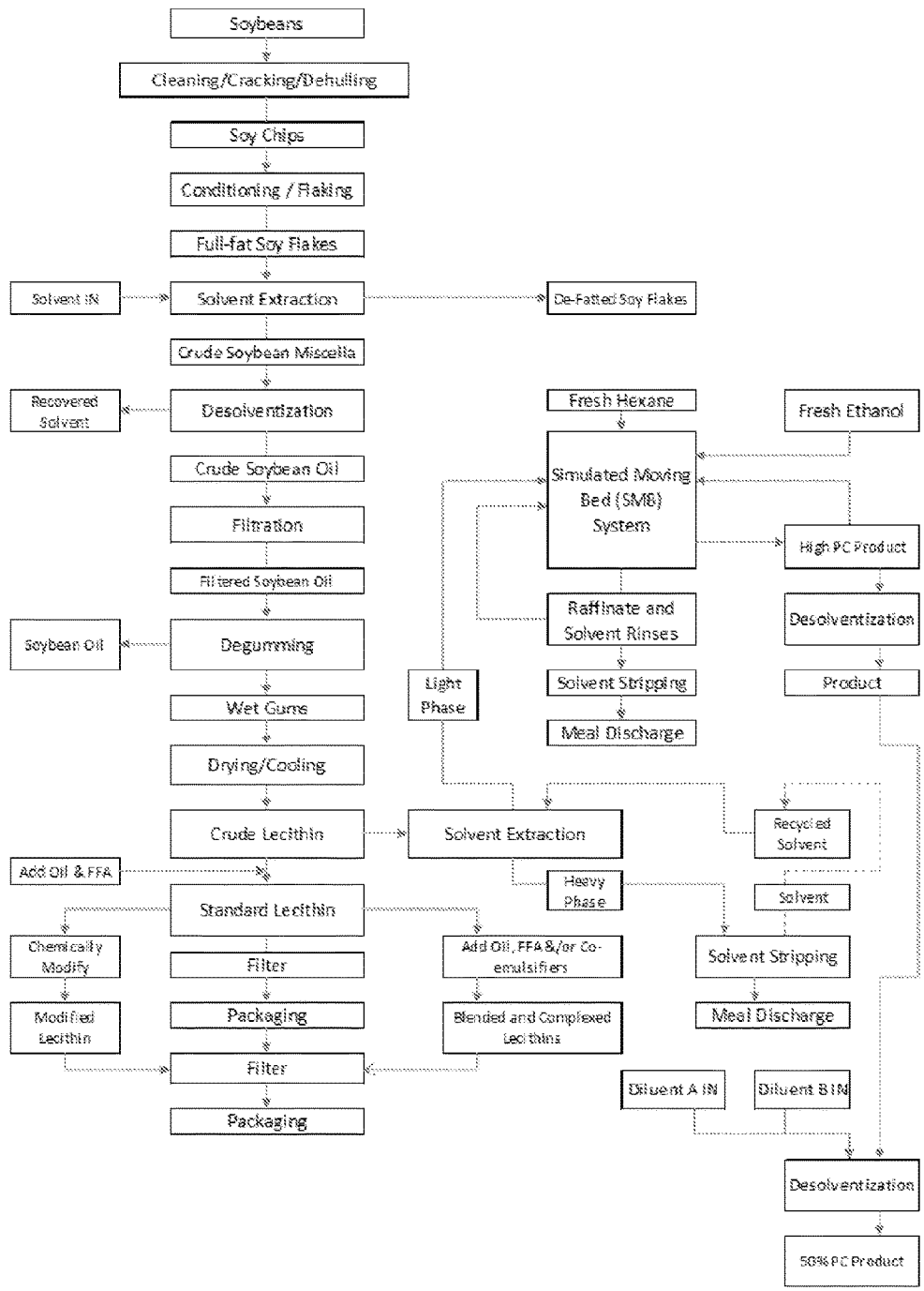
FIG. 1 is a flowchart of one embodiment of a process for fractionating phospholipids of the present invention.

In one embodiment, the phospholipid containing material originates from vegetable, i.e., soybean, processing. FIG. 1 illustrates a flowchart of one embodiment of a process used to obtain a phospholipid containing material and fractionate the phospholipids therefrom. Any of the various products of FIG. 1 that contain phospholipids and are capable of having the phospholipids fractionated or purified from the product using an adsorbent may be used in the processes of the present invention.

FIG. 1 also depicts one embodiment of the present invention where the phospholipid containing material comprises soy miscella, but in another embodiment, the phospholipid containing material may comprise crude lecithin. In FIG. 1, the soy miscella is mixed with the solvent, hexane or ethanol, and placed in contact with a resin to fractionate the phospholipids.

In FIG. 1, the soy miscella is obtained from the solvent extraction of full-fat soy flakes and may include soy oil, phospholipids, extraction solvent, other impurities extracted from the soybean along with the oil and solvent (i.e., possibly sugars from the soy and/or other solids from the soy flakes), and combinations of any thereof.

In various embodiments of FIG. 1, the different phospholipid containing material (i.e., soy miscella or crude lecithin) may use different resins and/or solvents to fractionate the phospholipids. For instance, in one embodiment, ethanol extracted soy miscella may be applied to a column (or simulated moving bed system) with a non-functional polystyrene resin, rinsed with ethanol, and eluted with hexane or hexane and ethanol. In another embodiment, crude lecithin extracted with hexane may be placed in contact with a non-functional phenolic based resin, rinsed with hexane, eluted with ethanol or a combination of ethanol with hexane, and rinsed with hexane. This embodiment may yield a fractionated product having at least 45% phosphatidyl choline.

In the various processes for fractionating phospholipids described herein, a solvent may be mixed with the phospholipid containing material to produce a feed. The feed may be placed in contact with the resin, wherein the resin associates with a phospholipid of the phospholipid containing material. The solvent may be: an alkane including, but not limited to, hexane, heptane, or a combination thereof an alcohol, water; or combinations of any thereof. The alcohol may be ethanol, isopropyl alcohol, beverage grade ethanol, denatured ethanol, or combinations of any thereof.

Figure 2:
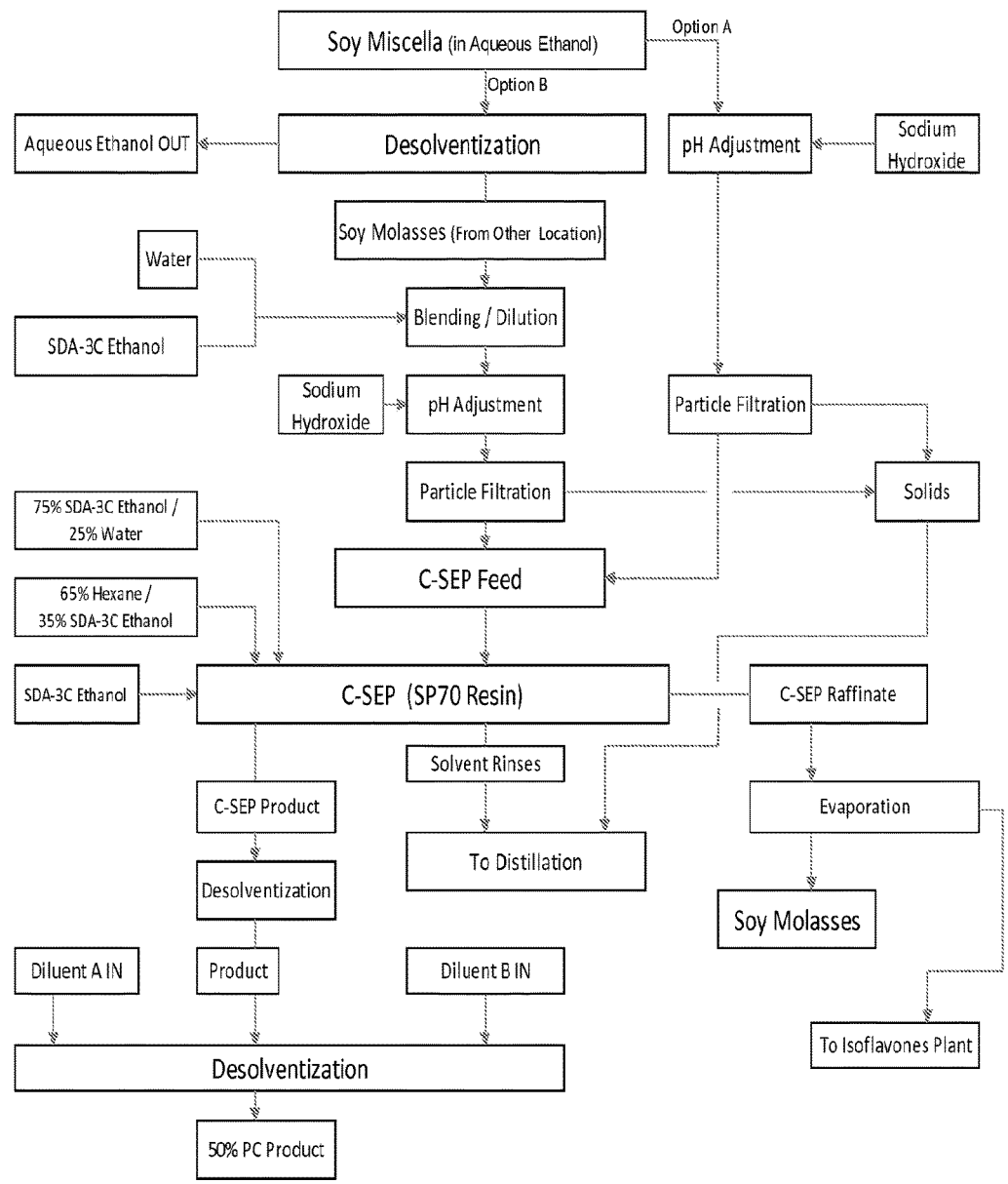
FIG. 2 is a flowchart of another embodiment of a process for fractionating phospholipids of the present invention.

In another embodiment shown in the flowchart of FIG. 2, the phospholipid containing material may be soy miscella (option A) or soy molasses (which may also be referred to as soy solubles) (option B). Soy solubles or soy molasses refers to a de-solventized aqueous ethanol extract (or desolventized and evaporated soy miscella) that may be obtained from the production of soy protein concentrate. In a further embodiment, the phospholipid containing material may be soy miscella which is in essence soy solubles or soy molasses that has not been de-solventized. Option A and option B are very similar, where option B adds water and ethanol to the soy molasses prior to pH adjustment.

In one embodiment, the phospholipid eluted from the adsorbent is collected. The phospholipid that is collected may be further purified, concentrated, or further processed to produce a finished product. The phospholipid may be eluted with an elution solvent. The elution solvent may be selected from the group consisting of: an alkane including, but not limited to, hexane, heptane, or a combination thereof water; an alcohol; or combinations of any thereof. The alcohol may be ethanol, isopropyl alcohol, beverage grade ethanol, denatured ethanol, or combinations of any thereof.

In one embodiment, the adsorbent or resin may be placed in a chromatography column where the phospholipid containing material or the feed is placed in contact with the resin. In such manner, a phospholipid, such as phosphatidyl choline (PC), phosphatidyl ethanolamine (PE), phosphatidyl inositol (PI), phosphatidic acid (PA), or combinations of any thereof, may associate with the resin and as a solvent or other liquid is run through the resin, other components of the phospholipid containing material or the feed are washed away from the phospholipid, thus, purifying or fractionating the phospholipid from the phospholipid containing material. In an additional embodiment, the resin may be placed into a simulated moving bed chromatography system.

The resin of the present invention may be a polymeric resin such as a non-ionic resin, a phenolic resin, a styrene resin, an acrylic resin, a cation-exchange resin, a weak-base resin, or combinations of any thereof.

In a further embodiment, a phospholipid containing material or a feed including the phospholipid containing material and/or a solvent may be pH adjusted such as to a pH of between 4.5-6.5, a pH of between 8.5-10.0, or a pH of between 9.0-9.5, and placed into contact with the resin. In other embodiments, the phospholipid containing material or a feed including the phospholipid containing material may have solids removed therefrom and placed into contact with the resin.

The following exemplary, non-limiting examples are provided to further describe the embodiments presented herein. Those having ordinary skill in the art will appreciate that variations of these Examples are possible within the scope of the invention.

Example 1

Adsorption and desorption of phospholipids was done on a Mitsubishi WK10 acrylic weak acid cation-exchange resin. 100 mls of the resin were loaded into a 15 mm diameter glass column. The resin was rinsed with 3 bed volumes (BV) of isopropyl alcohol (IPA), followed by rinsing the resin with 3 BV of hexane.

A feed was prepared by dissolving de-oiled soy lecithin in hexane at a 1:1 mass ratio. The feed was run over the resin in the 100 ml column. The basic load/elute test of this Example included 10 BV of the hexane/lecithin feed applied to the column, followed by 3 BV of hexane, followed by 3.5 BV of isopropyl alcohol. All runs were performed at 42° C. and a rate of 5 mls/minute. The column effluent was fractionated to determine the profile and the results of such fractionation are shown in Table 1. The column produced 1.16 grams of phosphatidyl choline (PC). A composite purity of the PC was calculated to be 82% as determined by dividing the total amount of PC by the sum of the PC, phosphatidyl ethanolamine (PE), and the phosphatidyl inositol (PI) represented by the following equation: PC/(PC+PE+PI).

TABLE 1

| Sample ID | PE mg/kg | PC mg/kg | PI mg/kg | Total mg/L | Total % | % PC |
|---|---|---|---|---|---|---|
| Feed | 105235 | 113199 | 60684 | 279118 | 27.9 | 41 |
| Raffinate & rinse | 86050 | 92192 | 48032 | 226274 | 22.6 | 41 |
| Product fraction 1 | 331 | 1113 | 25 | 1469 | 0.1 | 76 |
| Product fraction 2 | 4734 | 20193 | 0 | 24928 | 2.5 | 81 |
| Product fraction 3 | 568 | 3050 | 0 | 3618 | 0.4 | 84 |
| Product fraction 4 | 273 | 1529 | 13 | 1815 | 0.2 | 84 |
| Product fraction 5 | 97 | 900 | 26 | 1024 | 0.1 | 88 |

Figure 3:
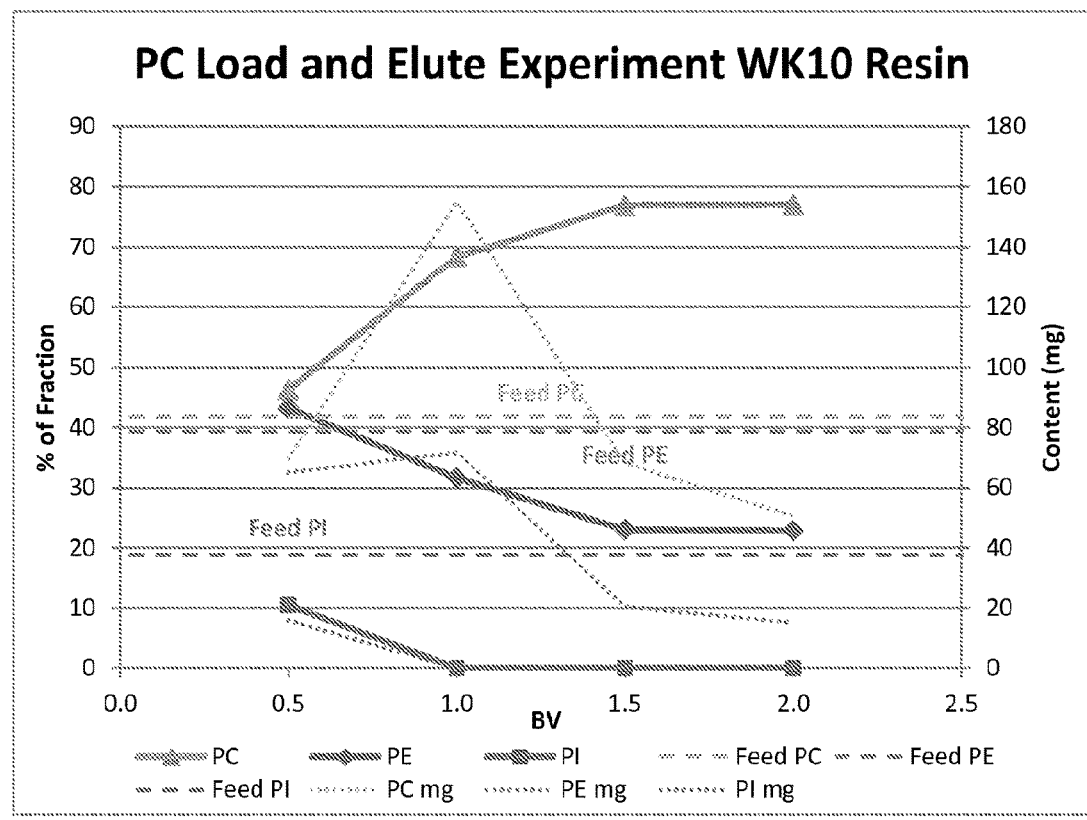
FIG. 3 shows a graph illustrating the ability of an embodiment of a process of the present invention to fractionate phospholipids.

The enhancement purity of the various phospholipids is shown in FIG. 3 and is represented by the percent of PC relative to the other phospholipids (PLs) in the column product obtained from a similar study.

Example 2

Figure 4:
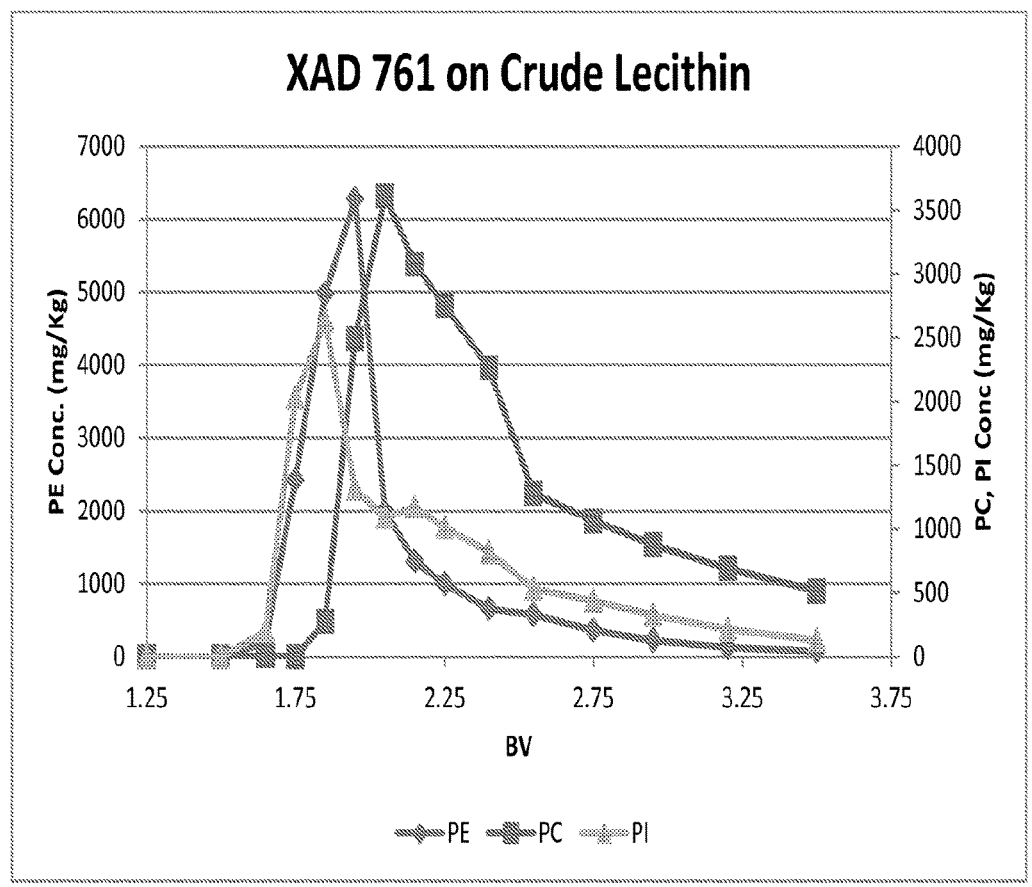
FIG. 4 shows another graph illustrating the ability of another embodiment of a process of the present invention to fractionate phospholipids.

Pulse testing for chromatographic separation of phospholipids was performed with Dow XAD761 non-functional phenolic resin (a phenol-formaldehyde condensate). 100 mls of the resin was loaded into a 15 mm glass column. The resin was washed with 3 BV of IPA followed by 3 BV of hexane. The feed was prepared by dissolving crude soy lecithin in hexane at a 1:1 mass ratio and mixing thoroughly. 2 mls of the feed was contacted with the 100 mls of the resin. After applying the feed to the resin, 1 BV of hexane was applied to the column and followed by 3.5 BV of an ethanol elution. This Example was performed at ambient temperature and a flow rate of 2.5 mls/minute. The effluent history of this Example is shown in FIG. 4.

Example 3

Figure 5:
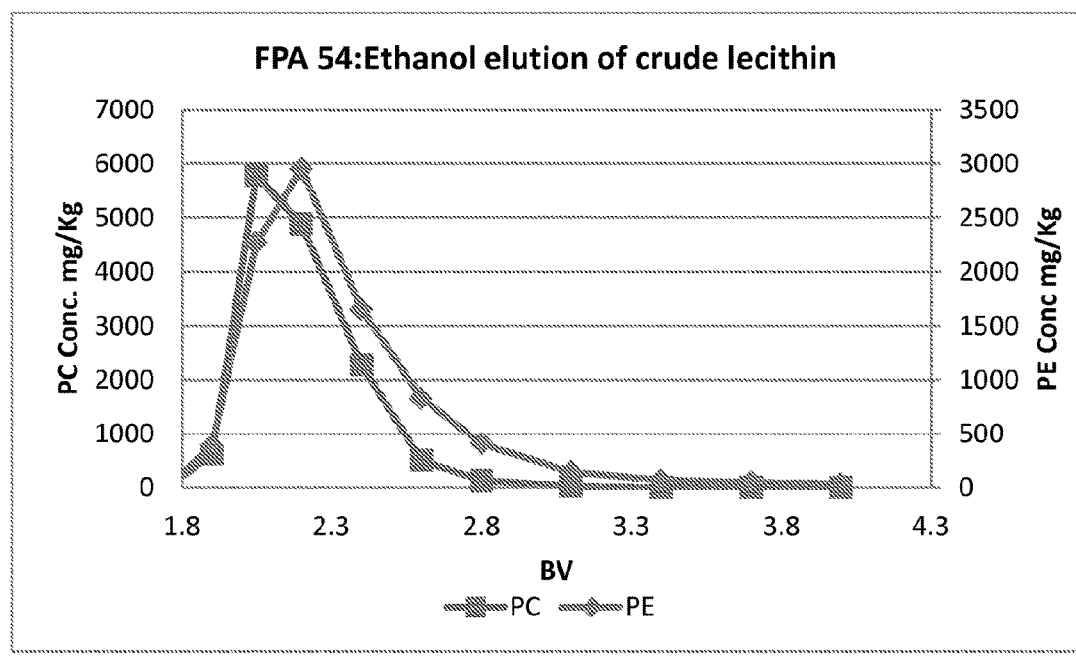
FIG. 5 shows an additional graph showing the ability of a further embodiment of a process of the present invention to fractionate phospholipids.

Affinity chromatography evaluation of the Dow FPA54 weak base phenolic resin (anion exchange resin based on phenol-formaldehyde matrix) on soy lecithin was performed. 100 mls of the resin was loaded into a 15 mm glass column and washed with 3 BV of IPA, followed by 3 BV of hexane. The feed was prepared by dissolving crude soy lecithin in hexane at a 2:1 mass ratio and thorough mixing. 2.5 mls of the feed was contacted with the 100 ml column of resin. After the feed was passed through the resin, 1.5 BV of hexane was passed over the column followed by 4 BV of ethanol. The Example was performed at ambient temperature and a flow rate of 2.5 mls/minute. The results indicate some separation of PC from the PE and the effluent history is shown in FIG. 5.

Example 4

Figure 6:
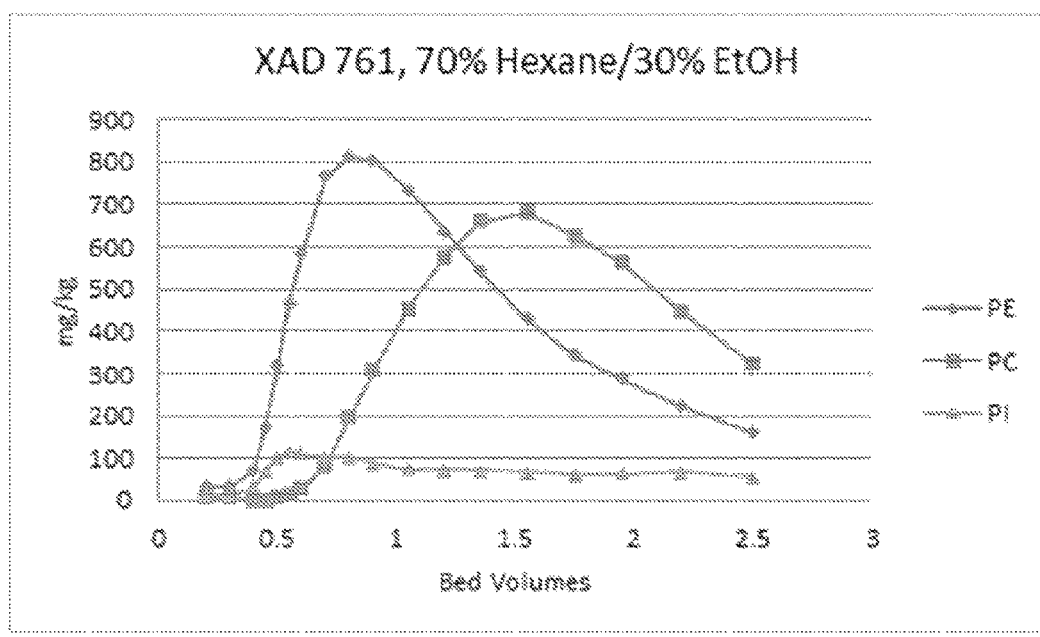
FIG. 6 depicts a graph showing the ability of yet another embodiment of a process of the present invention to fractionate phospholipids.

Lecithin paste was dissolved at a ratio of 50/50 in a solution of 70% hexane/30% ethanol. 10 mls of this feed was contacted with a Dow XAD761 non-functional phenolic resin, followed by a 70% hexane/30% ethanol mobile phase elution. The results of this Example are shown in FIG. 6 and show that there is a separation between PC and PE and PI.

Example 5

A solvent comprising 70% hexane/30% ethanol was prepared. This solvent was mixed with soy solubles at a ratio of 50/50 and mixed for 30 minutes. The solution was allowed to phase separate and the light (organic) phase was analyzed for phospholipid content. The results of such analysis are shown in Table 2. The results indicate a greater than 97% phospholipid extraction of the soy solubles.

TABLE 2

| 70/30 hexane/ethanol | Percent extracted | | | PC/(PC + PE + PI) |
|---|---|---|---|---|
| | PE | PC | PI | |
| Extract, % | 98.6 | 97.8 | 100.0 | — |
| Feed (ppm) | 6556 | 10162 | 7798 | 37% |
| Organic | 14137 | 15087 | 11843 | 37% |
| Aqueous | 202 | 346 | 0 | 63% |

Example 6

Figure 7:
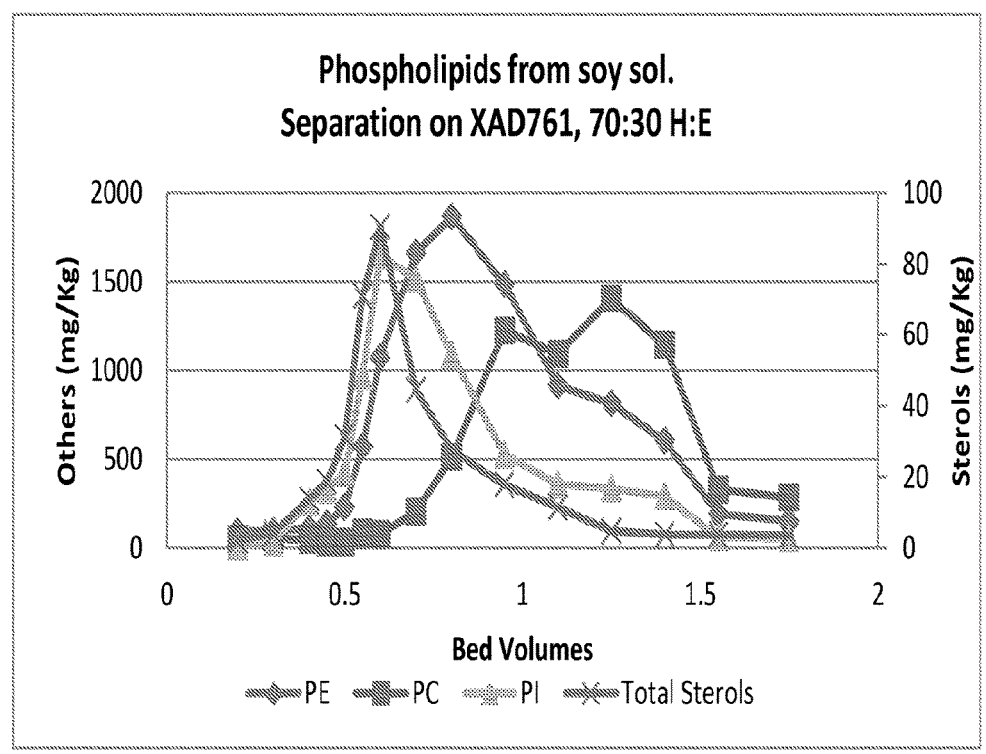
FIG. 7 is a graph showing the ability of one embodiment of the present invention to fractionate phospholipids and separate the phospholipids from sterols.

100 mls of Dow XAD761 was loaded into a 15 mm glass column and washed with 3 BV of 70% hexane/30% ethanol. A feed was prepared by extracting soy solubles (30% dry solids) with a 70% hexane/30% ethanol solution at a 1:1 ratio. A 5 ml pulse of the feed was contacted with the 100 ml column of resin, followed by 1.75 BV of 70% hexane/30% ethanol. The column was run at ambient temperature and a flow rate of 2.5 mls/minute. The results indicate a good separation of PC from the PE and PI, as well as a separation of the PC from sterols. The effluent history of this Example is shown in FIG. 7.

Example 7

Figure 8:
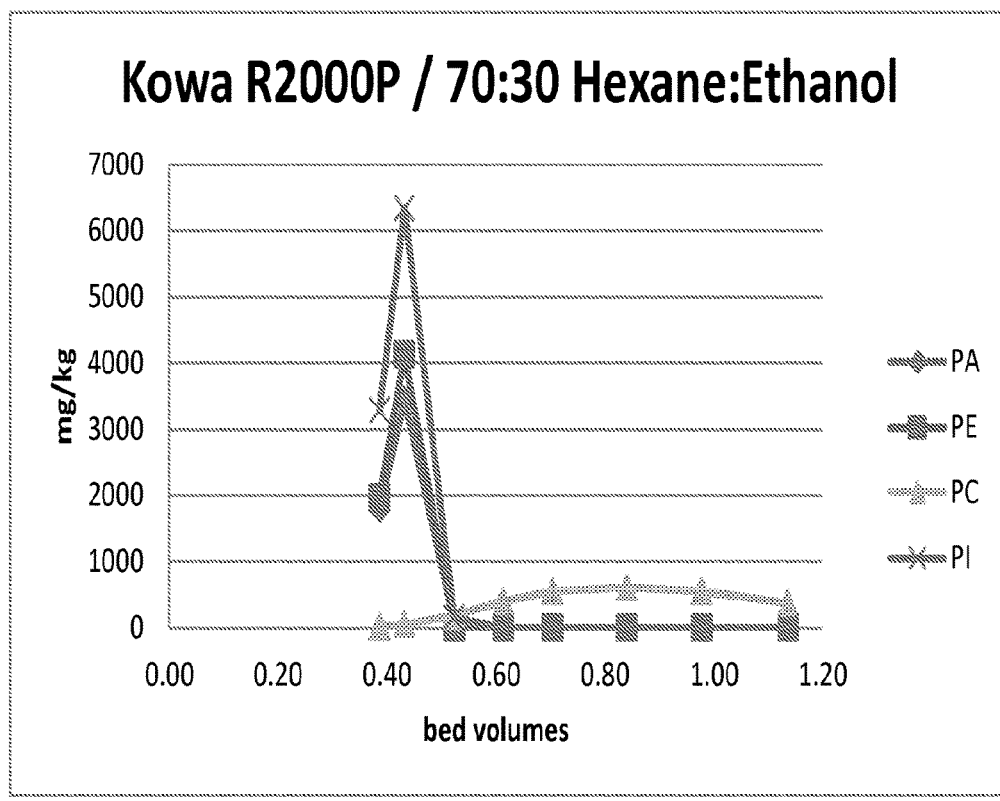
FIG. 8 shows a graph illustrating the ability of an embodiment of a process of the present invention to fractionate phospholipids.

330 mls of a Kowa R2000P (Bell Pearl) phenolic resin was slurried in 70% hexane/30% ethanol and loaded in a 25 mm glass column. The column was washed with 3 BV of 70% hexane/30% ethanol. A feed was prepared by mixing 10 parts soy solubles (60% dry solids), 5 parts hexane, 2.5 parts ethanol, and 2 parts deionized water. 10 ml of the feed was contacted with the resin, followed by 1.5 BV of 70% hexane/30% ethanol. The column was run at ambient temperature and a flow rate of 10 mls/minute. The results indicate a good separation of PC from PE and PI, and the effluent history is shown in FIG. 8.

Example 8

The separation and purification of PC with non-ionic adsorbents was evaluated. In this Example, soy miscella was used as feed. 400 mls of the Mitsubishi SP850 resin (a highly porous, styrenic adsorbent resin) was loaded into a 25 mm glass column and the resin was washed with 3 BV of 60% ethanol in water, followed by washing with 3 BV of 100% ethanol. The column was also rinsed with 60% ethanol in water. 13 BV of filtered soy miscella (about 6% dry solids) was passed through the resin column heated at 44° C. and the raffinate was collected. After running the soy miscella over the column, the heat was removed from the column and the rest of the Example was done at ambient temperature.

1 BV of 60% ethanol in water was passed through the resin column producing an effluent referred to as the rinse fraction. The resin column was eluted with 2 BV of ethanol and the collected product was referred to as the ethanol product. The resin column was contacted with 2BV of 80% hexane in ethanol producing an effluent referred to as the hexane product. The resin column was then rinsed with 1BV of 60% ethanol in water and the effluent was collected and referred to as the reset. The various effluents that were collected were analyzed for PA, PE, PC, and PI contents and the results are shown in Table 3.

TABLE 3

| Sample ID | PA mg/kg | PE mg/kg | PC mg/kg | PI mg/kg | Total mg/kg | PE + PC + PI Total % | % PC |
|---|---|---|---|---|---|---|---|
| Rinse fraction | 121 | 347 | 1219 | 84 | 1650 | 0.1650 | 74 |
| Raffinate | <LOD | <LOD | <LOD | 21 | 21 | 0.0021 | 0 |
| Ethanol product | 329 | 258 | 2829 | 421 | 3499 | 0.3499 | 81 |
| Hexane product | 1734 | 3373 | 10693 | 2516 | 16582 | 1.6582 | 64 |
| Reset | 659 | 597 | 502 | 1757 | 2856 | 0.2856 | 18 |

The results of this Example show good enrichment of PC as evidenced by the % PC as compared to the other phospholipids. The products obtained from this Example and 3 other similar phospholipid separations were de-solventized and analyzed. The resulting hexane product had a PC purity of 52.3% base on total solids, absolute purity, from feed miscella and an absolute purity of 3.1%. The results of such analysis are shown in Table 4.

TABLE 4

| | % solids | % PC solids basis | PC/PE ratio | % PLs solids basis | % others solids basis | PC yield, % |
|---|---|---|---|---|---|---|
| Soy miscella | 6.26 | 3.1 | 2.95 | 5.4 | 94.6 | — |
| Ethanol product | 7.1 | 21.1 | 5.98 | 27.8 | 72.2 | 25* |
| Hexane product | 75.7 | 52.3 | 2.62 | 91 | 9 | 75* |

*indicates the averages of four different column runs

Example 9

Figure 9:
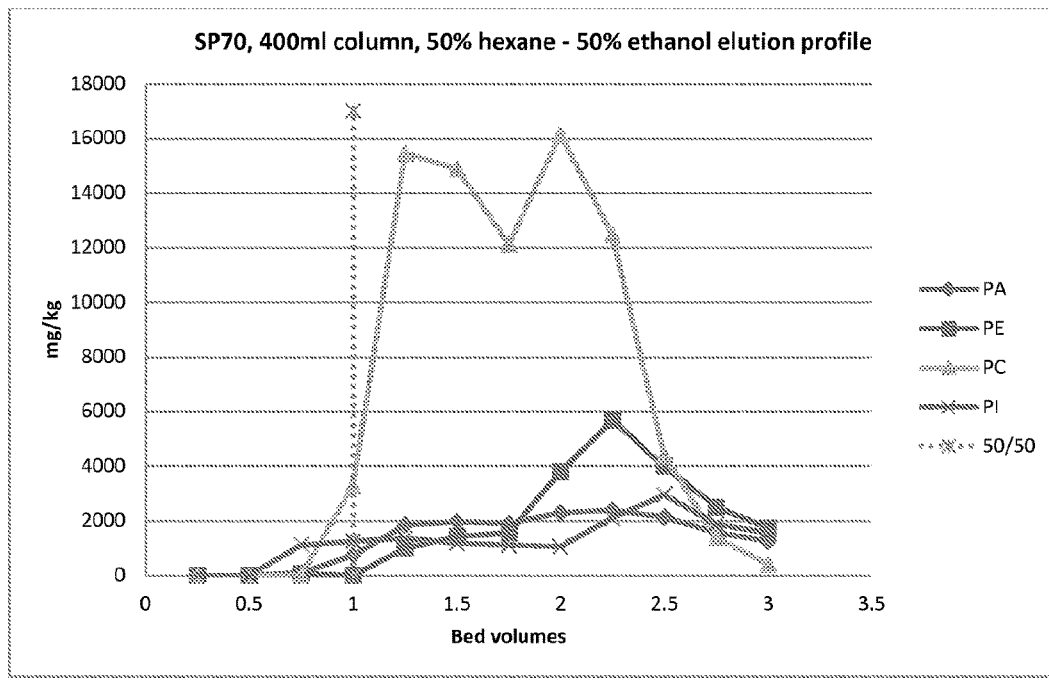
FIG. 9 depicts a graph showing the ability of yet another embodiment of a process of the present invention to fractionate phospholipids.

A 400 ml column of the Mitsubishi SP70 resin (a styrene-divinylbenzene resin) was set up using 50% hexane/50% ethanol as the eluent and soy miscella as the feed. Quarter bed volumes were collected and analyzed. The results are shown in FIG. 9. The amount of PC appears to be the highest between the first and second bed volumes. A portion of the effluent between the first and second bed volumes was analyzed and the results are shown in Table 5.

TABLE 5

| Phospholipid analyzed | % phospholipid |
|---|---|
| PC | 59.3 |
| PE | 7.8 |
| PI | 5.8 |
| PA | 8.4 |
| Total phospholipid | 81.3 |
| Non-phospholipid components | 18.7 |

Example 10

Figure 10:
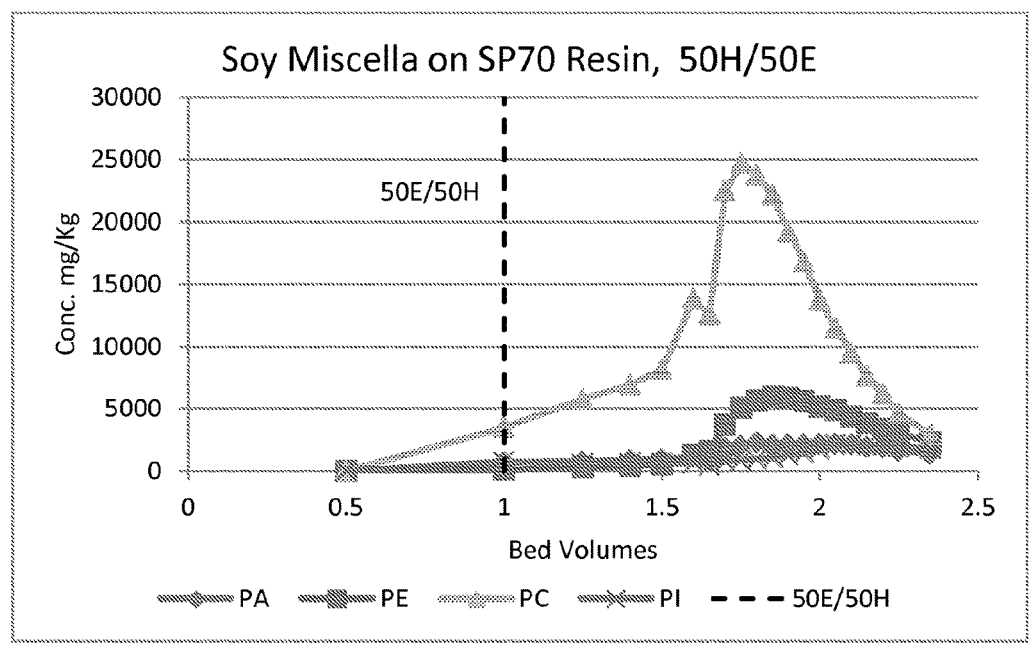
FIG. 10 shows another graph illustrating the ability of another embodiment of a process of the present invention to fractionate phospholipids.

100 mls of a Mitsubishi SP70 resin was loaded into a 15 mm glass column and washed with 3 BV of 60% ethanol in water, followed by washing with 1 BV of 100% ethanol. The column was also rinsed with 1 BV of 60% ethanol in water. 10 BV of a feed comprising filtered soy miscella (about 6% dry solids) was passed through the column at about 5 mls/minute at ambient temperature and the raffinate was collected. 1.5 BV of 60% ethanol was passed through the column and the collection of effluent fractions was started. After the 60% ethanol, 1 BV of 100% ethanol was passed through the column, followed by 1.5 BV of 50% hexane/50% ethanol. The elution profile is shown in FIG. 10.

Two 10 liter columns plumbed in series were set up and loaded with the Mitsubishi SP70 resin. The run conditions were substantially similar to those described above in reference to the 15 mm glass column. The products obtained from the two 10 liter columns, along with three other similar runs, were de-solventized and analyzed. The resulting hexane/ethanol product has a PC purity of 65% based on total solids. The results of the analysis are shown in Table 6.

TABLE 6

| Compound | Weight % |
|---|---|
| PC | 64.97 |
| Lyso PC | 0.57 |
| PE | 9.18 |
| LPE | 0.17 |
| APE | 1.79 |
| PI | 3.36 |
| PA | 5.99 |
| PG | 1.8 |
| Total phospholipids* | 87.83 |
| FFA | 3.13 |
| Moisture | 0.76 |
| Hydrolyzed amino acid | 0.3 |
| Free amino acid | 0.02 |
| MAB | 0.06 |
| Phytates | <20 ppm |
| TAG | <0.01 |
| Carbohydrates, below detection limit of 0.1 | <0.1 |
| Non-phospholipid components | 4.27 |

*phospholipid composition was determined by 31P-NMR.

Example 11

Figure 11:
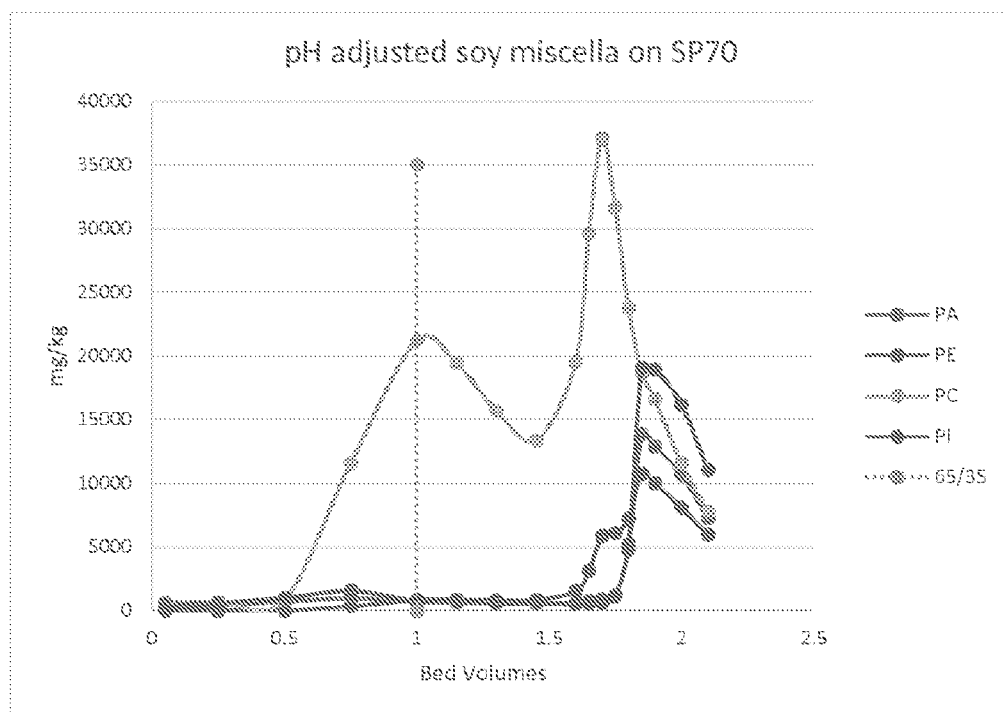
FIG. 11 is a graph showing the ability of one embodiment of the present invention to fractionate phospholipids.

100 mls of Mitsubishi SP70 resin were loaded into a 15 mm glass column, washed with 1 bed volume (BV) of specially denatured alcohol (SDA) 3C (formula of the denaturant), 190 proof (ethanol), followed by 1 BV of 65% hexane/35% SDA 3C, followed by 1 BV of SDA 3C, and followed by 1 BV of 75% SDA 3C. The feed was the supernatant from centrifuging soy miscella (6% dry solids) with the pH adjusted to 9 using 50% sodium hydroxide. 25 BV of the feed was passed through the resin in the column at 5 mls/minute at ambient temperature and the raffinate was collected. 1 BV of 75% ethanol was passed through the resin column, at which point the collection of the effluent fractions started. When the 75% SDA 3C rinse was complete, 1 BV of 100% SDA 3C, followed by 1.5 BV of 65% hexane/35% SDA 3C was passed through the column. The elution profile is shown in FIG. 11.

Example 12

80 gram portions of soy miscella were pH adjusted across a range of pH's from 1 to 10 using 0.1 M HCl or 0.1 M NaOH and measured using a pH probe. In a 100 ml jar, 50 ml of each pH adjusted soy miscella portion (pH of 1, 2, 3, 4, 5, 6, 7, 8, 9, and 10) was contacted with 10 grams of Mitsubishi SP70 resin and shaken occasionally at room temperature for 1 hour. After the hour, the liquid was decanted from each jar and sampled. To each jar, about 50 ml of 100% ethanol was added and the jar was allowed to stand for 20 minutes at room temperature with occasional mixing. After 20 minutes, the ethanol was decanted and sampled. The ethanol was replaced with hexane in the jars, and the jars were allowed to stand for 1 hour with occasional mixing. The hexane was decanted and sampled. All samples were analyzed for phospholipids. The resin which contacted the pH adjusted soy miscella whose pH was adjusted to 5 and 6 yielded the most PC, with the least amount of other phospholipids in the hexane washes.

Example 13

Figure 12:
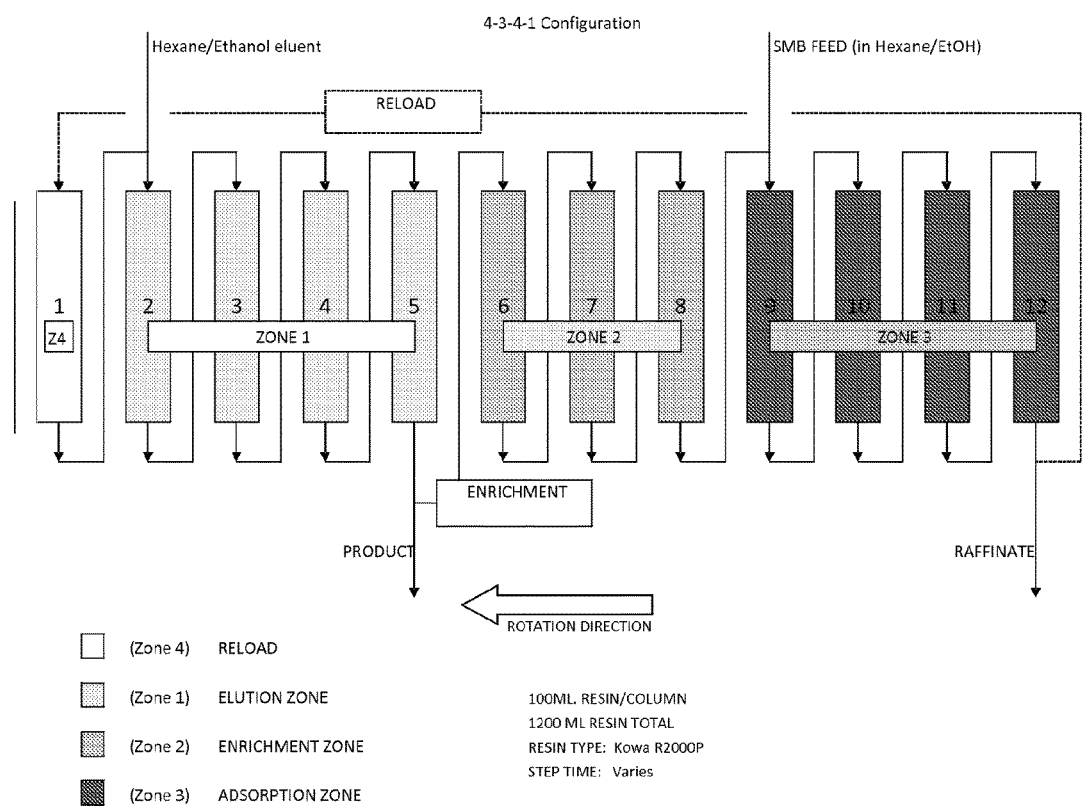
FIG. 12 illustrates one embodiment of a simulated moving bed chromatography system set-up to perform a process of fractionating phospholipids of the present invention.
Figure 13:
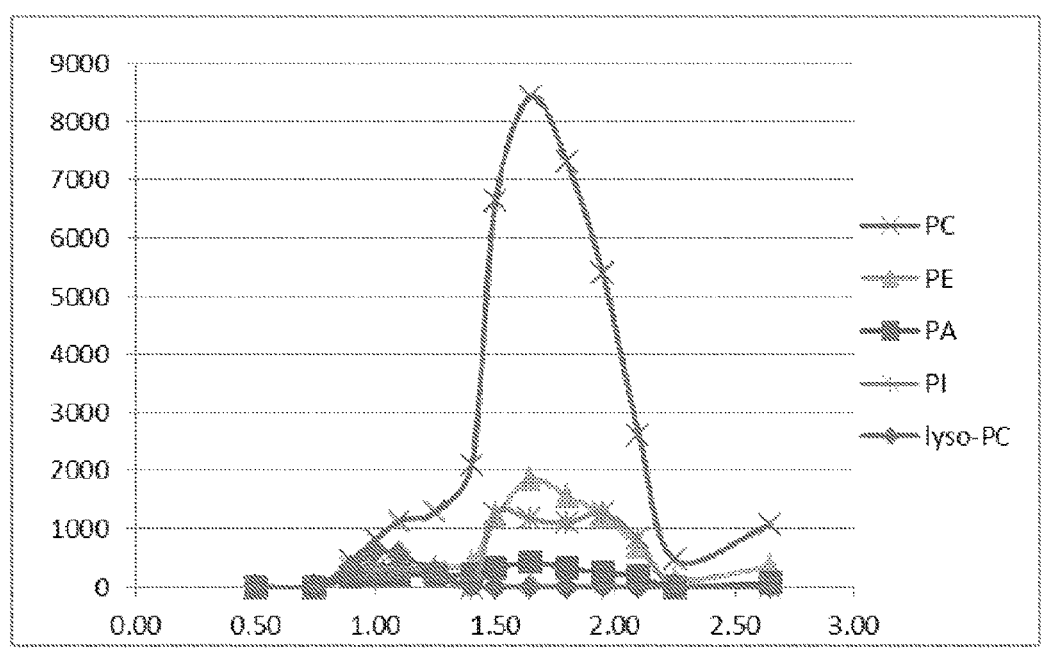
FIG. 13 is a graph showing the ability of another embodiment of the present invention to fractionate phospholipids. The x axis is Bed Volumes and the y axis is concentration of the phospholipids in mg/Kg.

Filtered soy miscella (having about 6% dry solids) was used as feed for this Example. The Kowa R2000P (Bell Pearl) phenolic resin was used in a carousel type simulated moving bed (SMB) system. The SMB used 12 100 ml resin columns and was configured in a 4-3-4-1 configuration as shown in FIG. 12. These conditions resulted in the system performance shown in Table 7.

TABLE 7

| Sample | PA mg/kg | PE mg/kg | PC mg/kg | PI mg/kg | Volume ml | Mass grams | PC purity % | PC Yield % |
|---|---|---|---|---|---|---|---|---|
| SMB Feed | 5685 | 6999 | 21979 | 7534 | — | — | 52.09 | — |
| SMB Product | 0 | 28 | 708 | 0 | 420 | 296.9 | 96.16 | 84.65 |
| SMB Raffinate | 604 | 609 | 300 | 827 | 180 | 127.3 | — | — |

The best results from this Example were obtained with the following conditions. Step Time: 5.6 minutes. Feed Rate: 1.0 mls/minute. Enrichment Rate: 7.0 mls/minute. Elution Rate: 17.1 mls/minute. Reload Rate: 2.9 mls/minute.

The ratios of PC to the other phospholipids indicate the degree of separation achieved with the Kowa resin in a continuous SMB operation. The feed had a PC ratio to the other three phospholipids of approximately 3:1, while the product has 25:1 (PC/PE ratio) to over 100:1 (PC/PA, PC/PI ratios) PC ratio. These ratios are shown in Table 8.

TABLE 8

| Sample | PC/PA Ratio | PC/PE Ratio | PC/PI Ratio |
|---|---|---|---|
| SMB Feed | 3.87 | 3.14 | 2.92 |
| SMB Product | >100 | 25.07 | >100 |
| SMB Raffinate | 0.50 | 0.49 | 0.36 |

Example 14

50 gram portions of crude soy lecithin were contacted with ethanol and pH adjusted across a range of 2 to 13 using 0.1 M HCl or 0.1 M NaOH. In a 250 mL jar, 100 mL of pH adjusted beverage grade ethanol was added to 50 g each of the crude lecithin and shaken occasionally at room temperature for 10 minutes. After settling for several minutes, the light liquid phase was decanted from each jar and sampled. After settling, the heavy residue phase was also sampled. The extraction results ranges from 18% to 26% where the best results appeared to be obtained (in terms of % PC extracted and a ratio of PC/PA) at an ethanol pH of about 13.2. Conditions of the reactions and the results are presented in Tables 9 and 10.

TABLE 9

| Sample ID | | PA (g) | % | PE (g) | % | PC(g) | % | PI(g) | % | I-PC (g) | % | Purity (%) | PC/PE | PC/PA |
|---|---|---|---|---|---|---|---|---|---|---|---|---|---|---|
| 67-B1 | lecithin | 2.838 | | 8.187 | | 8.879 | | 3.712 | | 0.315 | | 37.60 | 1.08 | 3.13 |
| 67-E1 | pH? | 0.14 | 4.9 | 0.487 | 5.9 | 1.585 | 17.8 | 0.059 | 1.58 | 0.124 | 39.31 | 69.8 | 3.26 | 11.34 |
| 67-R1 | pH? | 2.913 | | 7.581 | | 7.082 | | 3.972 | | 0.253 | | 32.9 | 0.93 | 2.43 |
| | (%) = | 108.00 | | 99.00 | | 98.00 | | 109.00 | | 120.00 | | | | |
| 67-B2 | lecithin | 2.854 | | 8.235 | | 8.93 | | 3.734 | | 0.316 | | 37.60 | 1.08 | 3.13 |
| 67-E2 | pH = 13.21 | 0.161 | 5.6 | 0.544 | 6.6 | 1.62 | 18.1 | 0.073 | 1.96 | 0.122 | 38.43 | 67.6 | 2.98 | 10.06 |
| 67-R2 | pH = 13.21 | 2.737 | | 6.753 | | 6.236 | | 3.81 | | 0.216 | | 31.9 | 0.92 | 2.28 |
| | (%) = | 102.00 | | 89.00 | | 88.00 | | 104.00 | | 107.00 | | | | |
| 67-B3 | lecithin | 2.853 | | 8.231 | | 8.927 | | 3.732 | | 0.316 | | 37.60 | 1.08 | 3.13 |
| 67-E3 | pH = 13.12 | 0.235 | 8.2 | 0.698 | 8.5 | 2.419 | 27.1 | 0.044 | 1.18 | 0.122 | 38.43 | 71.2 | 3.46 | 10.3 |
| 67-R2 | pH = 13.12 | 3.057 | | 7.469 | | 6.881 | | 3.896 | | 0.235 | | 32.3 | 0.92 | 2.25 |
| | (%) = | 115.00 | | 99.00 | | 104.00 | | 106.00 | | 113.00 | | | | |
| 67-B4 | lecithin | 2.857 | | 8.244 | | 8.941 | | 3.738 | | 0.317 | | 37.60 | 1.08 | 3.13 |
| 67-E4 | pH = 12.76 | 0.183 | 6.4 | 0.49 | 5.9 | 1.684 | 18.8 | 0 | 0 | 0.112 | 35.23 | 69.7 | 3.44 | 9.2 |
| 67-R4 | pH = 12.76 | 2.709 | | 6.815 | | 6.83 | | 0 | | 0.221 | | 34.7 | 1 | 2.52 |
| | (%) = | 101.00 | | 89.00 | | 95.00 | | 0.00 | | 105.00 | | | | |
| 67-B5 | lecithin | 2.837 | | 8.186 | | 8.877 | | 3.711 | | 0.315 | | 37.60 | 1.08 | 3.13 |
| 67-E5 | pH = 2.85 | 0.202 | 7.1 | 0.514 | 6.3 | 2.042 | 23 | 0.051 | 1.37 | 0.109 | 34.75 | 72.7 | 3.97 | 10.11 |
| 67-R5 | pH = 2.85 | 2.633 | | 6.79 | | 5.596 | | 3.513 | | 0.183 | | 30.2 | 0.82 | 2.13 |
| | (%) = | 100.00 | | 89.00 | | 86.00 | | 96.00 | | 93.00 | | | | |
| 67-B6 | lecithin | 2.869 | | 8.277 | | 8.976 | | 3.753 | | 0.318 | | 37.60 | 1.08 | 3.13 |
| 67-E6 | pH = 3.83 | 0.204 | 7.1 | 0.515 | 6.2 | 1.99 | 22.3 | 0.053 | 1.42 | 0.132 | 41.46 | 72.1 | 3.88 | 9.79 |
| 67-R6 | pH = 3.83 | 2.69 | | 7.53 | | 6.84 | | 3.516 | | 0.207 | | 33.2 | 0.91 | 2.54 |
| | (%) = | 101.00 | | 97.00 | | 98.00 | | 95.00 | | 107.00 | | | | |
| 67-B7 | lecithin | 2.843 | | 8.204 | | 8.897 | | 3.72 | | 0.315 | | 37.60 | 1.08 | 3.13 |
| 67-E7 | pH = 6.7 | 0.273 | 9.6 | 0.739 | 9 | 2.332 | 26.2 | 0.042 | 1.12 | 0.103 | 32.53 | 68.9 | 3.16 | 8.55 |
| 67-R7 | pH = 6.7 | 2.723 | | 6.888 | | 6.687 | | 3.659 | | 0.253 | | 33.5 | 0.97 | 2.46 |
| | (%) = | 105.00 | | 93.00 | | 101.00 | | 99.00 | | 113.00 | | | | |

TABLE 10

| Sample ID | | PA (g) | % | PE (g) | % | PC(g) | % | PI(g) | % | I-PC (g) | % | Purity (%) | PC/PE | PC/PA |
|---|---|---|---|---|---|---|---|---|---|---|---|---|---|---|
| Feed | lecithin | 2.838 | | 8.187 | | 8.879 | | 3.712 | | 0.315 | | 37.60 | 1.08 | 3.13 |
| Light Phase | pH? | 0.14 | 4.9 | 0.487 | 5.9 | 1.585 | 17.8 | 0.059 | 1.58 | 0.124 | 39.31 | 69.8 | 3.26 | 11.34 |
| Heavy Phase | pH? | 2.913 | | 7.581 | | 7.082 | | 3.972 | | 0.253 | | 32.9 | 0.93 | 2.43 |
| Amount accounted for | | 108.00 | | 99.00 | | 98.00 | | 109.00 | | 120.00 | | | | |
| Feed | lecithin | 2.854 | | 8.235 | | 8.93 | | 3.734 | | 0.316 | | 37.60 | 1.08 | 3.13 |
| Light Phase | pH = 13.21 | 0.161 | 5.6 | 0.544 | 6.6 | 1.62 | 18.1 | 0.073 | 1.96 | 0.122 | 38.43 | 67.6 | 2.98 | 10.06 |
| Heavy Phase | pH = 13.21 | 2.737 | | 6.753 | | 6.236 | | 3.81 | | 0.216 | | 31.9 | 0.92 | 2.28 |
| Amount accounted for | | 102.00 | | 89.00 | | 88.00 | | 104.00 | | 107.00 | | | | |
| Feed | lecithin | 2.853 | | 8.231 | | 8.927 | | 3.732 | | 0.316 | | 37.60 | 1.08 | 3.13 |
| Light Phase | pH = 13.12 | 0.235 | 8.2 | 0.698 | 8.5 | 2.419 | 27.1 | 0.044 | 1.18 | 0.122 | 38.43 | 71.2 | 3.46 | 10.3 |
| Heavy Phase | pH = 13.12 | 3.057 | | 7.469 | | 6.881 | | 3.896 | | 0.235 | | 32.3 | 0.92 | 2.25 |
| Amount accounted for | | 115.00 | | 99.00 | | 104.00 | | 106.00 | | 113.00 | | | | |
| Feed | lecithin | 2.857 | | 8.244 | | 8.941 | | 3.738 | | 0.317 | | 37.60 | 1.08 | 3.13 |
| Light Phase | pH = 12.76 | 0.183 | 6.4 | 0.49 | 5.9 | 1.684 | 18.8 | 0 | 0 | 0.112 | 35.23 | 69.7 | 3.44 | 9.2 |
| Heavy Phase | pH = 12.76 | 2.709 | | 6.815 | | 6.83 | | 0 | | 0.221 | | 34.7 | 1 | 2.52 |

TABLE 10-continued

| Sample ID | | PA (g) | % | PE (g) | % | PC(g) | % | PI(g) | % | I-PC (g) | % | Purity (%) | PC/PE | PC/PA |
|---|---|---|---|---|---|---|---|---|---|---|---|---|---|---|
| Amount accounted for | | 101.00 | | 89.00 | | 95.00 | | 0.00 | | 105.00 | | | | |
| Feed | lecithin | 2.837 | | 8.186 | | 8.877 | | 3.711 | | 0.315 | | 37.60 | 1.08 | 3.13 |
| Light Phase | pH = 2.85 | 0.202 | 7.1 | 0.514 | 6.3 | 2.042 | 23 | 0.051 | 1.37 | 0.109 | 34.75 | 72.7 | 3.97 | 10.11 |
| Heavy Phase | pH = 2.85 | 2.633 | | 6.79 | | 5.596 | | 3.513 | | 0.183 | | 30.2 | 0.82 | 2.13 |
| Amount accounted for | | 100.00 | | 89.00 | | 86.00 | | 96.00 | | 93.00 | | | | |
| Feed | lecithin | 2.869 | | 8.277 | | 8.976 | | 3.753 | | 0.318 | | 37.60 | 1.08 | 3.13 |
| Light Phase | pH = 3.83 | 0.204 | 7.1 | 0.515 | 6.2 | 1.99 | 22.3 | 0.053 | 1.42 | 0.132 | 41.46 | 72.1 | 3.88 | 9.79 |
| Heavy Phase | pH = 3.83 | 2.69 | | 7.53 | | 6.84 | | 3.516 | | 0.207 | | 33.2 | 0.91 | 2.54 |
| Amount accounted for | | 101.00 | | 97.00 | | 98.00 | | 95.00 | | 107.00 | | | | |
| Feed | lecithin | 2.843 | | 8.204 | | 8.897 | | 3.72 | | 0.315 | | 37.60 | 1.08 | 3.13 |
| Light Phase | pH = 6.7 | 0.273 | 9.6 | 0.739 | 9 | 2.332 | 26.2 | 0.042 | 1.12 | 0.103 | 32.53 | 68.9 | 3.16 | 8.55 |
| Heavy Phase | pH = 6.7 | 2.723 | | 6.888 | | 6.687 | | 3.659 | | 0.253 | | 33.5 | 0.97 | 2.46 |
| Amount accounted for | | 105.00 | | 93.00 | | 101.00 | | 99.00 | | 113.00 | | | | |

Figure 14:
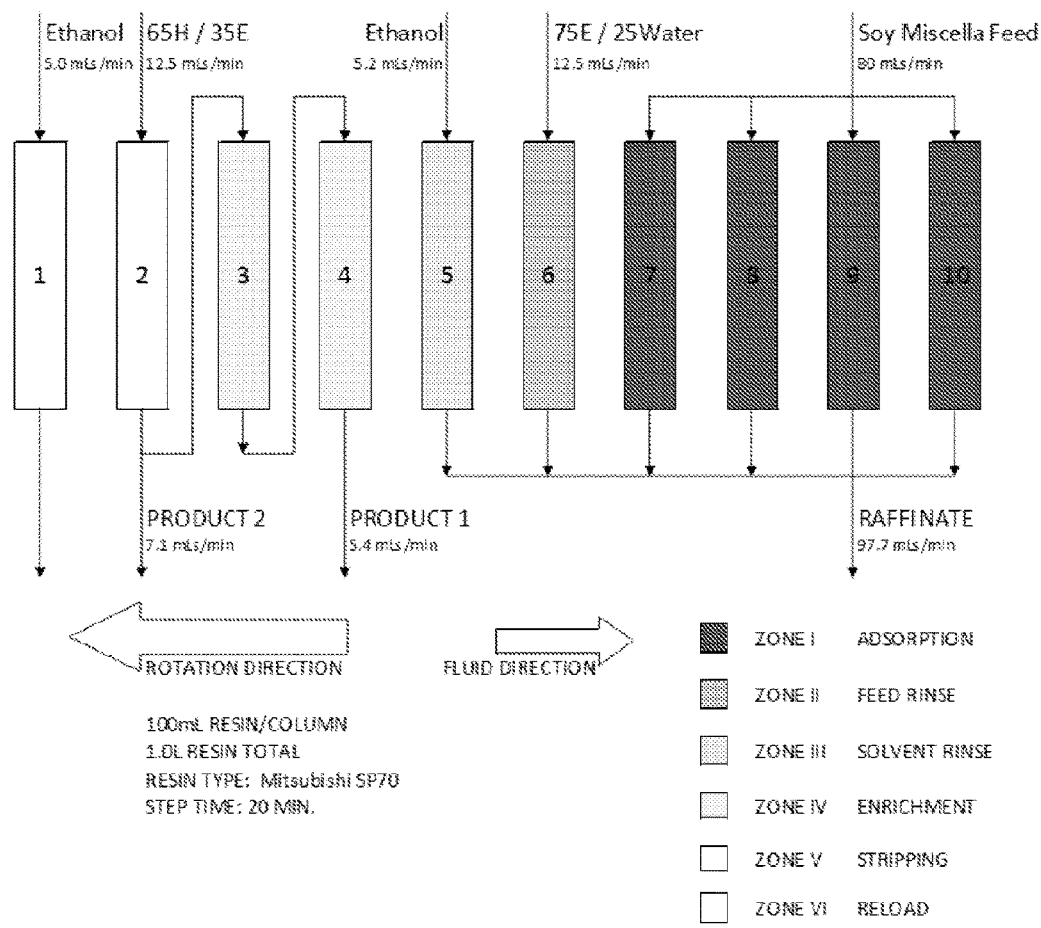
FIG. 14 illustrates another embodiment of a simulated moving bed chromatography system set-up to perform a process of fractionating phospholipids of the present invention.

Example 15 pH adjusted portions of crude (unfiltered) soy lecithin were contacted with wet denatured ethanol. The extraction was performed similar to Example 14 to obtain a light phase and a heavy phase. In this Example, 50 mL of the light phase was used as the feed (the pH adjusted crude lecithin in wet denatured ethanol) and was loaded at 5 mL/min. and ambient temperature onto a 15 mm glass column containing 100 mL of Mitsubishi SP 70 brand resin in wet denatured ethanol. The eluent was collected as raffinate 1. 1 BV of 60% wet denatured ethanol in water was run and the eluent was collected as raffinate 2. Once the 60% wet denatured ethanol rinse was completed, 1 BV of wet denatured ethanol, followed by a 1.5 BV of 80:20 hexane:wet denatured ethanol mixture was passed through the column to waste. The elution profile is shown in the graph of FIG. 14. The PC/PA ratio from 1.5 to 2.0 BV was greater than 20.

Example 16

A C-SEP system was set up, loaded with Mitsubishi SP70 resin, configured in a 1-1-2-1-1-4 configuration as shown in FIG. 14. Soy miscella feed was pH adjusted to 9 using 50% NaOH, followed by settling. The liquid portion of this soy miscella (having about 6% dry solids) was used as feed for this Example. The conditions resulted in the system performance shown in Table 11.

TABLE 11

| Sample | PA mg/kg | PE mg/kg | PC mg/kg | PI mg/kg | PC/PA Ratio | Mass grams | PC purity % S. B. | PC Yield % |
|---|---|---|---|---|---|---|---|---|
| SMB Feed | 299 | 430 | 1473 | 467 | 4.92 | 4005 | 3.12 | — |
| SMB Prod 1 | 612 | 2956 | 18789 | 924 | 30.68 | 268 | 69.54 | 85.38 |
| SMB Prod 2 | 803 | 1880 | 948 | 1201 | 1.18 | 260 | 15.39 | — |

Example 17

Figure 15:
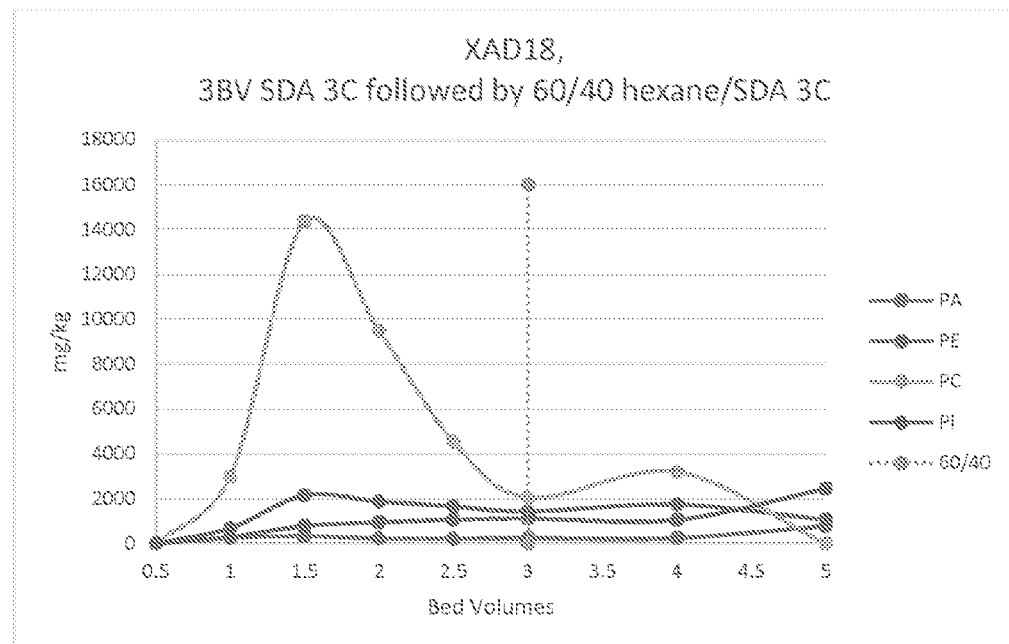
FIG. 15 depicts a graph showing the ability of one embodiment of the present invention to fractionate phospholipids.

100 mls of Dow XAD18 resin were loaded into a 15 mm glass column, washed with 1BV of SDA 3C, 190 proof (ethanol), followed by 1 BV of 60% SDA 3C. 15 BV of the feed was passed through the resin in the column at 5 mls/minute at 40° C., followed by 1 BV of 60 SDA 3C. The column was eluted with 3 BV of 100% SDA 3C and 0.5 BV fractions were collected. The elution was completed with 2 BV of 60% hexane/40% SDA 3C and 1 BV fractions were collected. The elution profile is shown in FIG. 15. 85% of the PC elutes with the SDA 3C with the PC/PA ratio being 25.2.

Example 18

58 kilograms of PC C-SEP product at approximately 2%-2.5% solids were collected into five 5 gallon partially filled buckets. Collectively, the buckets contained 967.3 grams of phospholipids, 733.6 grams of which were PC. A precipitate forms in the product upon exiting the C-SEP. The amount of the precipitate is small and is 60% phospholipids, however only 0.33% of the precipitate is PC. The liquid portion PC C-SEP product is then concentrated to approximately 10% solids and collected into a single 5 gallon bucket. Upon sitting at least 24 hours, a second precipitate forms. The second precipitate which accounts for about 1% of the mass is 75% phospholipids with 12% of the precipitate being PC. The liquid portion is then concentrated to approximately 50% solids. The 50% solids concentrate weighs 1.7 kg and contains 784.1 grams of phospholipids of which 656.4 grams are PC. No further precipitation is observed. Removing the precipitates in stages can be used to enhance the overall PC purity of the final product. Table 12 illustrates the purity enhancement. PC purity on a phospholipid basis is PC/PC+PA+PE+PI.

TABLE 12

| | PC/PA | PC/PE | PC purity on a phospholipid basis |
|---|---|---|---|
| PC CSEP PD (2% solids) | 15.9 | 5.7 | 75.84 |
| First Evap PD (10% solids) | 21.5 | 6.1 | 81.05 |
| Second Evap PD (50% solids) | 25.5 | 7.9 | 83.72 |

Example 19

Figure 16:
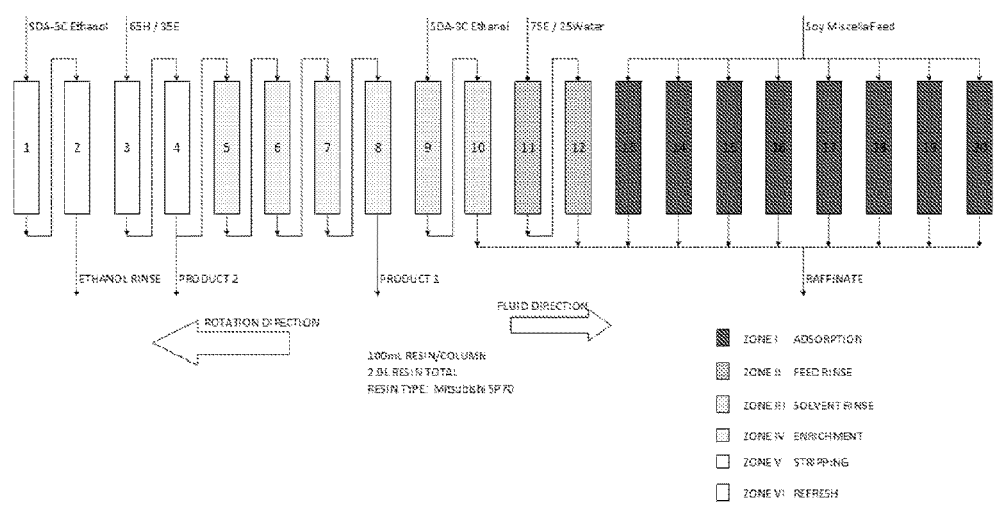
FIG. 16 shows an additional embodiment of a simulated moving bed chromatography system set-up to perform a process of fractionating phospholipids of the present invention.

In this example, the chromatographic system using Mitsubishi SP70 Non-ionic resin is configured in a 2-2-4-2-2-8 sequence in a simulated moving bed (SMB) apparatus. There is twenty (20) 100 mL columns, for a total resin volume of 2.0 liters. Zone I is the adsorption zone; zone II is the Feed Rinse zone; zone III is the Solvent Rinse Zone, zone IV is the Enrichment Zone; zone V is the Solvent Stripping zone, and zone VI is the Reload zone (FIG. 16). The SMB apparatus contains 20 columns on a carousel, and provisions for rotating the columns in the direction opposite the flow of fluid at defined intervals, called the "Step Time". The step time is 20 minutes.

Zone I (the Adsorption Zone) is defined by the feed (Soy Miscella) inlet ports, all plumbed to run in parallel; and there is 8 columns in this zone (columns 13-20 in FIG. 16). Soy miscella feed containing ~0.1-0.2% PC is applied continuously in this zone; where, the phospholipids are preferentially adsorbed onto the resin, while most of the other solids in stream continue through the resin bed and are discharged in the raffinate port.

Zone II (the Feed Rinse zone) is columns 11 & 12 in FIG. 16. The solvent flow in this zone is a solution of 75% SDA-3C ethanol/25% water (150 proof), and there is be two columns in this zone. The primary purpose of this zone is to ensure the removal of the feed impurities from the void fraction within the resin bed, and to rinse the resin.

Zone III (the Solvent Rinse zone) is columns 9 & 10 in FIG. 16. There is two columns in this zone, as well. The primary purpose of this zone is to remove the bulk of the water from the mobile phase, using 190 proof SDA-3C ethanol, prior to the hexane elution zone.

Zone IV (the Enrichment Zone) is the zone defined by the product 2 discharge and Enrichment inlet ports (columns 5-8 in FIG. 16). The primary purpose of this zone is to separate the adsorbed phospholipids to enhance the purity of PC relative to the PE, PI, and PA.

Zone V (Solvent Stripping zone) is the zone defined by the 65/35 Hexane/Ethanol rinse inlet and the Product 2 (P2) outlet (Columns 3 & 4 in FIG. 16). The purpose of this zone is to strip the remaining phospholipids off the resin to prepare it for adsorption.

Zone VI (the Reload zone) is columns 1 & 2 in FIG. 16. The purpose of this zone is to remove the hexane from the resin bed prior to returning the columns to the adsorption zone. This is important because hexane in the resin bed will cause a decrease in adsorption of phospholipids, when the column rotates into the adsorption zone.

Example 20. 2-Step Chromatography for High Purity PC

In this example, the process involves a two-step chromatographic separation to produce a product of >90% PC purity. Between the two steps there is a solvent removal step and a solvent addition step prior to the second stage chromatographic system. The first stage chromatographic system can be either the styrene based resin (such as SP70) using miscella/molasses/light phase from ethanol extracted lecithin (EEL) as feed; or the phenolic based resin (such as XAD761) using the light phase of hexane extracted lecithin (HEL) as feed. The primary product from any of these processes can be further processed using a further embodiment of the process. In this case the product is exposed to further purification as described in FIG. 18 above. The specifics for this processing are detailed herein.

Figure 17:
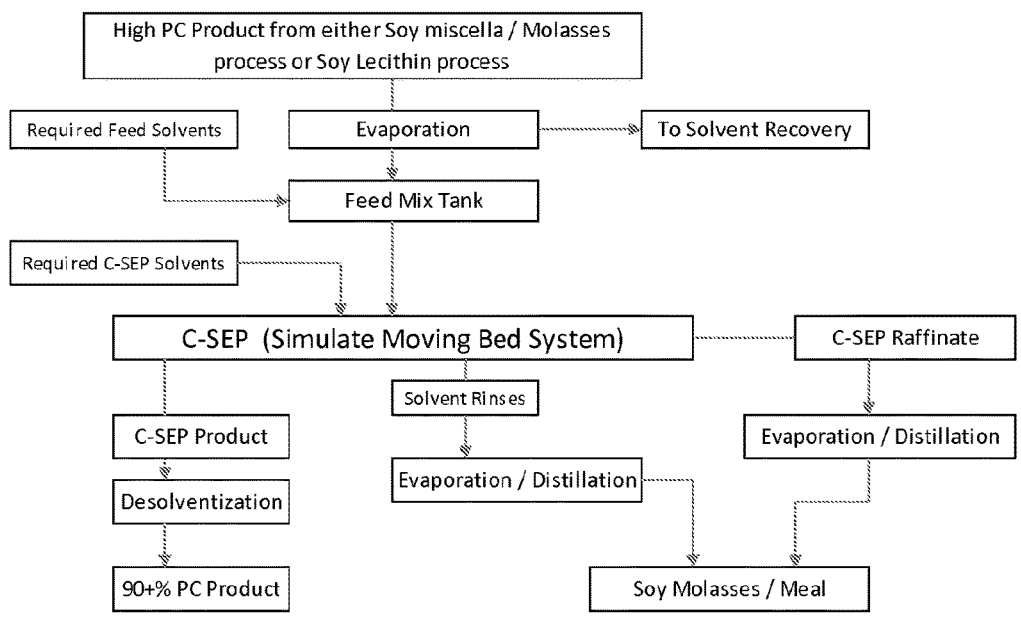
FIG. 17 is a flowchart of a two-stage process of an embodiment of fractionating phospholipids of the present invention.

For the product from any of these processes as feed, the adsorbent could be either the phenolic based resin or the styrene based resin. In the event that the phenolic based resin (XAD761, Bellpearl, or similar) is used, the required feed solvent (FIG. 17) is hexane. The solvents required in the chromatographic operation are a hexane rinse with ethanol elution (or a combination of ethanol and hexane), followed by a hexane rinse. If the non-ionic styrene based resin (SP70) resin is used, the required feed solvent (FIG. 17) would be ethanol and water (to approximately 60% ethanol/35% water). The solvents required in the chromatographic operation are the ethanol/water rinse, followed by ethanol rinse; followed by hexane/ethanol elution, followed by an ethanol rinse.

The present invention has been described with reference to certain exemplary and illustrative embodiments, compositions and uses thereof. However, it will be recognized by persons having ordinary skill in the art that various substitutions, modifications or combinations of any of the exemplary embodiments may be made without departing from the scope of the invention. Thus, the invention is not limited by the description of the exemplary and illustrative embodiments, but rather by the appended claims.

What is claimed is:

1. A process of fractionating phospholipids, the process comprising:
   mixing a solvent with a phospholipid containing material, thus producing a feed;
   placing the feed in contact with an adsorbent, such that the adsorbent associates with at least one phospholipid of the phospholipid containing material;
   eluting the at least one phospholipid from the adsorbent with an elution solvent;
   collecting the eluted, at least one phospholipid and the elution solvent;
   allowing a precipitate to form in the eluted, at least one phospholipid and the elution solvent;
   removing the precipitate from the eluted, at least one phospholipid and the elution solvent; and
   concentrating the at least one phospholipid in the elution solvent;
   wherein the adsorbent is a polymeric resin.

2. The process according to claim 1, wherein the polymeric resin is selected from the group consisting of a phenolic resin, a styrene resin, a non-ionic resin, an acrylic resin, a cation-exchange resin, a weak-base resin, and combinations of any thereof.

3. The process according to claim 1, wherein the phospholipid containing material is selected from the group consisting of miscella, molasses, lecithin, and combinations of any thereof.

4. The process according to claim 1, further comprising eluting the at least one phospholipid from the adsorbent.

5. The process according to claim 4, wherein eluting the at least one phospholipid from the adsorbent comprises contacting an elution solvent with the adsorbent.

6. The process according to claim 4, further comprising:
   placing the at least one phospholipid eluted from the adsorbent in contact with a second adsorbent; and
   mixing the at least one phospholipid eluted from the adsorbent with a solvent before placing in contact with the second absorbent.

7. The process according to claim 1, wherein the solvent is selected from the group consisting of an alcohol, an alkane, water, and combinations of any thereof.

8. The process according to claim 1, wherein the at least one phospholipid is selected from the group consisting of phosphatidyl choline (PC), phosphatidyl ethanolamine (PE), phosphatidyl inositol (PI), phosphatidic acid (PA), and combinations of any thereof.

9. The process according to claim 1, further comprising extracting the phospholipid containing material from a phospholipid source.

10. The process according to claim 1, further comprising adjusting a pH of the phospholipid containing material to a pH of between 8.5-10.0.

11. The process according to claim 1, further comprising removing solids from the phospholipid containing material.

12. The process according to claim 7, wherein the solvent is the alkane and is selected from the group consisting of hexane, heptane, or a combination thereof.

13. A process of fractionating phospholipids, the process comprising:

mixing a phospholipid containing material selected from the group consisting of miscella, lecithin, molasses, and combinations of any thereof with a solvent, thus producing a feed;

placing the feed in contact in contact with a polymeric resin, such that the polymeric resin associates with at least one phospholipid of the phospholipid containing material; and eluting the at least one phospholipid from the polymeric resin with an elution solvent;

collecting the eluted, at least one phospholipid and the elution solvent;

allowing a precipitate to form in the eluted, at least one phospholipid and the elution solvent;

removing the precipitate from the eluted, at least one phospholipid and the elution solvent; and concentrating the at least one phospholipid in the elution solvent.

14. The process of claim 13, wherein the polymeric resin is selected from the group consisting of a phenolic resin and a styrene resin.

15. The process of claim 13, wherein the solvent comprises an alcohol, an alkane, water, and combinations of any thereof.

16. The process of claim 13, wherein the phospholipid containing material is the miscella.

* * * * *